US008747381B2

(12) United States Patent
Nagai

(10) Patent No.: US 8,747,381 B2
(45) Date of Patent: Jun. 10, 2014

(54) SPECIMEN CONTAINER

(75) Inventor: Takaaki Nagai, Kobe (JP)

(73) Assignee: Sysmex Corporation, Kobe (JP)

( * ) Notice: Subject to any disclaimer, the term of this patent is extended or adjusted under 35 U.S.C. 154(b) by 403 days.

(21) Appl. No.: 12/685,429

(22) Filed: Jan. 11, 2010

(65) Prior Publication Data

US 2010/0114056 A1 May 6, 2010

Related U.S. Application Data

(63) Continuation of application No. PCT/JP2008/062147, filed on Jul. 4, 2008.

(30) Foreign Application Priority Data

Jul. 12, 2007 (JP) ............................ JP2007-183747

(51) Int. Cl.
*A61B 19/00* (2006.01)

(52) U.S. Cl.
USPC .......................................................... 604/414

(58) Field of Classification Search
USPC ......................................... 604/403, 411, 415
See application file for complete search history.

(56) References Cited

U.S. PATENT DOCUMENTS

| | | | | |
|---|---|---|---|---|
| 4,210,418 | A | 7/1980 | Brown et al. | |
| 6,056,925 | A | 5/2000 | Sarstedt | |
| 6,382,442 | B1 * | 5/2002 | Thibault et al. | 215/249 |
| 2003/0004390 | A1 * | 1/2003 | Matsunaga et al. | 588/252 |
| 2006/0076258 | A1 * | 4/2006 | Pencoske | 206/459.5 |

FOREIGN PATENT DOCUMENTS

| | | |
|---|---|---|
| EP | 539 141 A1 | 4/1993 |
| EP | 0 901 822 A2 | 3/1999 |
| JP | 59-024388 | 6/1984 |
| JP | 61-043541 | 12/1986 |
| JP | 05-036364 | 5/1993 |
| JP | 05-026530 | 7/1993 |
| JP | 06-170249 | 6/1994 |
| JP | 07-270411 | 10/1995 |
| JP | 11-151214 | 8/1999 |
| JP | 2000-506419 | 5/2000 |

OTHER PUBLICATIONS

English translation of JP 5-26530 A to Asanuma.*
English translation, JP 61-43541 A to Takizawa et al.*
International Search Report for International Application No. PCT/JP2008/062147, dated Sep. 16, 2008, 2 pages.

* cited by examiner

*Primary Examiner* — Melanie Hand
(74) *Attorney, Agent, or Firm* — Brinks Gilson & Lione

(57) ABSTRACT

A specimen container includes a specimen storing portion for storing a specimen, wherein the specimen storing portion is provided with an opening on an upper end, a sealing member for sealing the opening, wherein the sealing member is enabled to be passed through by a suction tube for sucking a specimen stored in the specimen storing portion, and a cylindrical portion having a predetermined height to allow insertion of the suction tube, wherein the cylindrical portion is arranged in series with the specimen storing portion on a side provided with the opening.

12 Claims, 10 Drawing Sheets

SPECIMEN CONTAINER

RELATED APPLICATIONS

This application is a continuation of PCT/JP2008/062147 filed on Jul. 4, 2008, which claims priority to Japanese Application No. JP2007-183747 filed on Jul. 12, 2007. The entire contents of these applications are incorporated herein by reference.

BACKGROUND OF THE INVENTION

1. Field of the Invention

The present invention relates to a specimen container for storing a specimen such as blood employed in the field of clinical tests or the like, and more particularly, it relates to a specimen container storing a small quantity of specimen such as a control sample employed for quality control of an automatic analyzer.

2. Description of the Background Art

Specimen measurement from transport of a specimen to pretreatment and multiple measurement has become automated with recent increase in the measurement number of patient specimens in the field of clinical tests. Measurement of a control sample for performing quality control of an automatic analyzer also has become automated.

In a case where quality control is performed in an automatic analyzer such as an automatic blood cell counter, a control sample such as control blood is stored in a predetermined specimen container to be used. The specimen container storing the control sample is placed on a specimen rack together with a plurality of specimen containers storing the patient specimens and is provided to the automatic analyzer. A bar code label for identifying the patient specimen is stuck on each specimen container storing the patient specimen, and a bar code label for identifying the control sample is stuck on the specimen container storing the control sample. The bar codes of these bar code labels stuck on the specimen containers are read by a bar code reader of the automatic analyzer, and it is identified whether the specimen stored in the specimen container is the patient specimen or the control sample.

At the time of measurement, in order to uniformly disperse components such as blood cells in the specimen container, the blood cells and the like in the specimen container are stirred. Thereafter, a suction tube is inserted into the specimen container, and sample suction and component measurement such as counting of the blood cells are performed.

A small quantity of the control sample is enough as the quantity of the specimen required for the measurement as compared with that of the patient specimen, and hence a volume of a normal specimen container is too large for the quantity of the control sample. Thus, when the control sample stored in the normal specimen container is stirred, the moving quantity of the control sample in the specimen container is increased. Consequently, there is a possibility that the specimen is damaged. The control sample is used (measured) a plurality of times dissimilarly to the patient specimen measured only once. Thus, the control sample is damaged due to stirring at the plurality of times, and this can greatly affect quality of the control sample. The volume of the specimen container is large as compared with the quantity of the control sample, and hence the rate of the control sample adhering and remaining on an inner surface of the specimen container is increased. Consequently, the stirring is conceivably insufficient.

When the specimen container itself is downsized depending on the quantity of the control sample, on the other hand, the size of the specimen container is different from that of the normal specimen container, and hence there is a possibility that a measuring operation such as stirring or suction can not be performed in a manner similar to that of the normal specimen container storing the patient specimen. Thus, an inconvenience that the control sample can not be automatically measured is caused. Further, an area for sticking the bar code label on an outer side surface of the specimen container can not be ensured, and whether the specimen stored in the specimen container is the patient specimen or the control sample can not be automatically identified by the bar code. This also makes automatic analysis difficult.

Japanese Utility Model Laying-Open No. 5-36364 discloses an invention of a “specimen container” as a container for storing a small quantity of specimen. This specimen container is a specimen container constituted by a cap and a cylindrical container body opened/closed by the cap and having an outer shape similar to the normal specimen container, in which a bottom of the container body is formed in the middle of the cylindrical body. In other words, the specimen container has a so-called push-up bottom, and the volume of storing the sample is smaller than that of the normal specimen container. According to this structure, the moving quantity of the sample in the specimen container is small even when a small quantity of the specimen is stored and stirred, and hence damage to the specimen is reduced. The outer shape of the specimen container is not downsized, and hence the specimen in the specimen container can be stirred in a manner similar to that performed for the normal specimen container by the automatic analyzer, and the area for sticking the bar code label can be ensured on the outer side surface.

In the aforementioned specimen container described in Japanese Utility Model Laying-Open No. 5-36364, however, while the specimen in the specimen container can be stirred in the manner similar to that performed for the normal specimen container and the bar code label can be stuck, the specimen container is formed to have the push-up bottom shape and hence a forward end of the suction tube may collide with the push-up bottom portion when the suction tube is inserted from above by the automatic analyzer. In order to avoid such a problem, means for adjusting a depth for inserting the suction tube depending on the shape of the specimen container is required and a structure of the analyzer is complicated.

Thus, in a case of a small quantity of the specimen sample, reduction in the volume of the specimen container is demanded in order not to damage and ununiformly stir the specimen sample. Further, the depth of the specimen container must be ensured so as not to collide with the bottom portion of the suction tube, while ensuring a height enough to smoothly perform the operation such as stirring by the automatic analyzer. The specimen container satisfying all of these demands is desired.

SUMMARY OF THE INVENTION

The present invention has been proposed in order to solve the aforementioned problem, and an object of the present invention is to provide a specimen container for storing a small quantity of specimen such as a control sample and suitable for measurement by an automatic analyzer.

A specimen container according to a first aspect of the present invention comprises a specimen storing portion for storing a specimen, wherein the specimen storing portion is provided with an opening on an upper end, a sealing member for sealing the opening, wherein the sealing member is enabled to be passed through by a suction tube for sucking a specimen stored in the specimen storing portion, and a cylindrical portion having a predetermined height to allow insertion of the suction tube, wherein the cylindrical portion is arranged in series with the specimen storing portion on a side provided with the opening.

A specimen container according to a second aspect of the present invention is a specimen container for storing a specimen analyzed by an analyzer, wherein the specimen container is formed in a cylindrical shape having a bottom portion, and a sealing member for sealing a specimen stored in the specimen container is arranged on a predetermined position between an upper end and a bottom portion of the specimen container.

As hereinabove described, this specimen container according to the first aspect is provided with the specimen storing portion provided with the opening on the upper end and enabled to store the specimen, the sealing member sealing the opening and enabled to be passed through by the suction tube for sucking the specimen stored in the specimen storing portion, and the cylindrical portion arranged in series with the specimen storing portion on the opening side of the specimen storing portion and having the predetermined height to allow insertion of the suction tube, whereby the sealing member sealing the specimen storing portion is arranged on a prescribed position between the upper end and the bottom portion of the specimen container, and hence a sealing volume where the specimen is stored can be reduced as compared with the overall volume of the specimen container. Thus, the moving quantity of the specimen in the container is reduced even when stirring the specimen in a state where a small quantity of the specimen is stored in the specimen container, and hence damage to the specimen by stirring is reduced and stirring of the specimen can be prevented from ununiformity. The specimen container is so formed that an overall height of the specimen container is a height of a normal specimen container by adjusting the height of the cylindrical portion, and hence an operation such as stirring by the analyzer can be performed in a manner similar to the operation for the normal specimen container, and an sufficient region for sticking an bar code label on an outer side surface can be ensured. The specimen container according to the present invention has a sufficient depth from the upper end to the bottom portion dissimilarly to a push-up bottom, and hence the suction tube can be inhibited from colliding with the bottom portion even when suction is performed in a manner similar to the operation for the normal specimen container. Consequently, the specimen container suitable for automatic analysis by the automatic analyzer can be provided.

DETAILED DESCRIPTION OF THE PREFERRED EMBODIMENTS

Embodiments of the present invention will be hereinafter described with reference to drawings.

First Embodiment

A specimen container 110 according to a first embodiment of the present invention will be now described with reference to FIGS. 1 to 3 and FIGS. 9 to 11.

Figure 1:
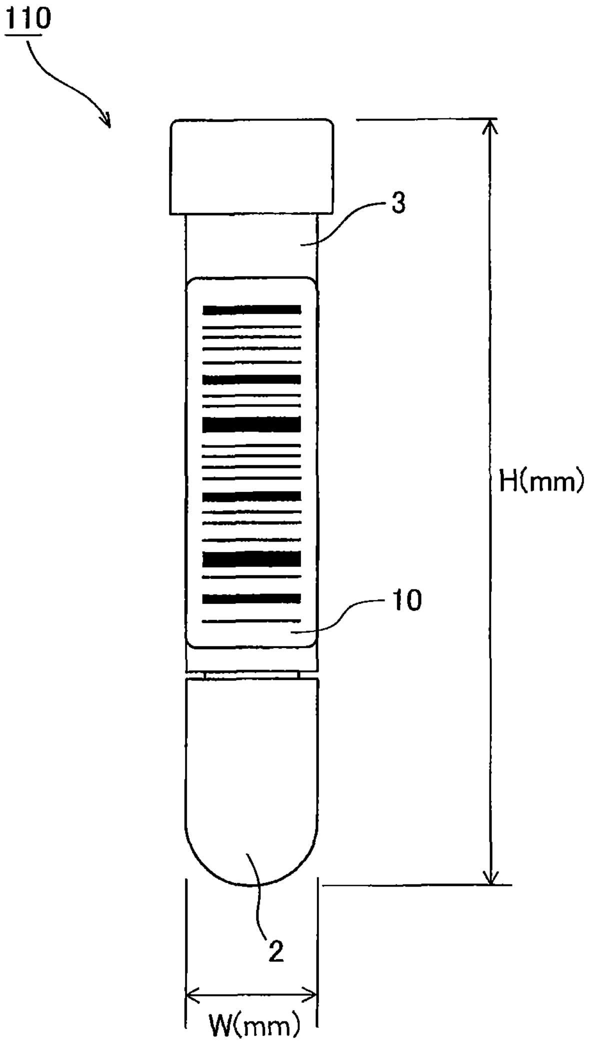
[FIG. 1] A front elevational view showing appearance of a specimen container according to a first embodiment of the present invention.

The specimen container 110 according to the first embodiment of the present invention is a specimen container storing a specimen such as a control sample 200 (see FIG. 3), and has test tube-shaped appearance, as shown in FIG. 1. The specimen container 110 comprises a container body 2 including a bottom portion 2*b*, a cylindrical body 3 capable of coupling with the container body 2 and a sealing member 4, as shown in FIG. 2.

Figure 3:
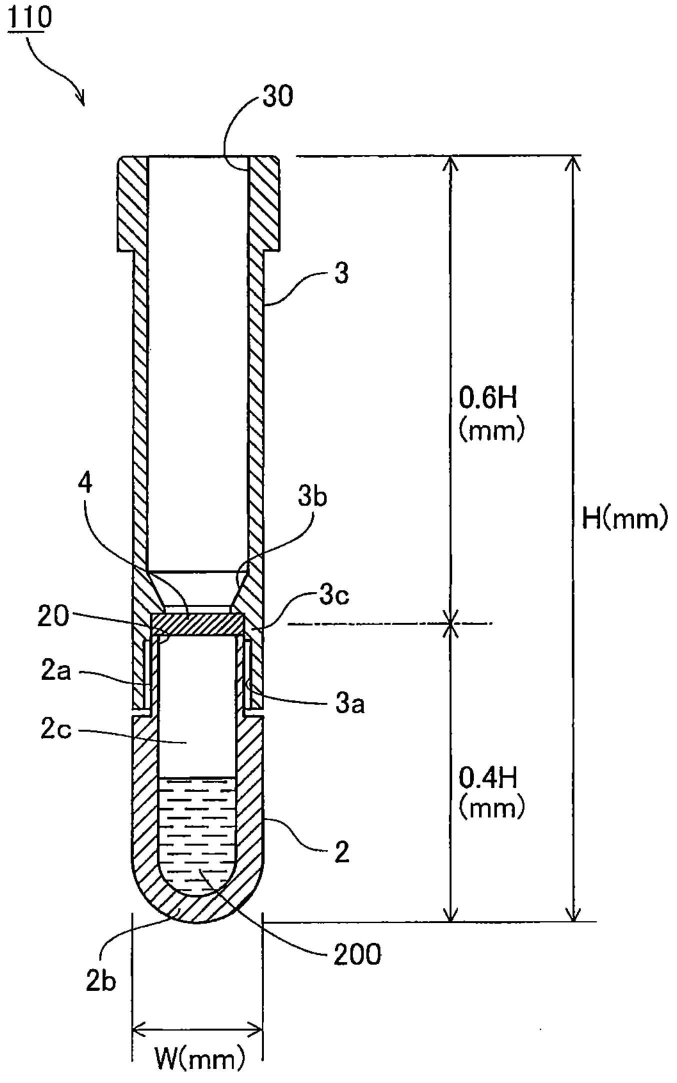
[FIG. 3] A sectional view of the specimen container according to the first embodiment of the present invention.
Figure 9:
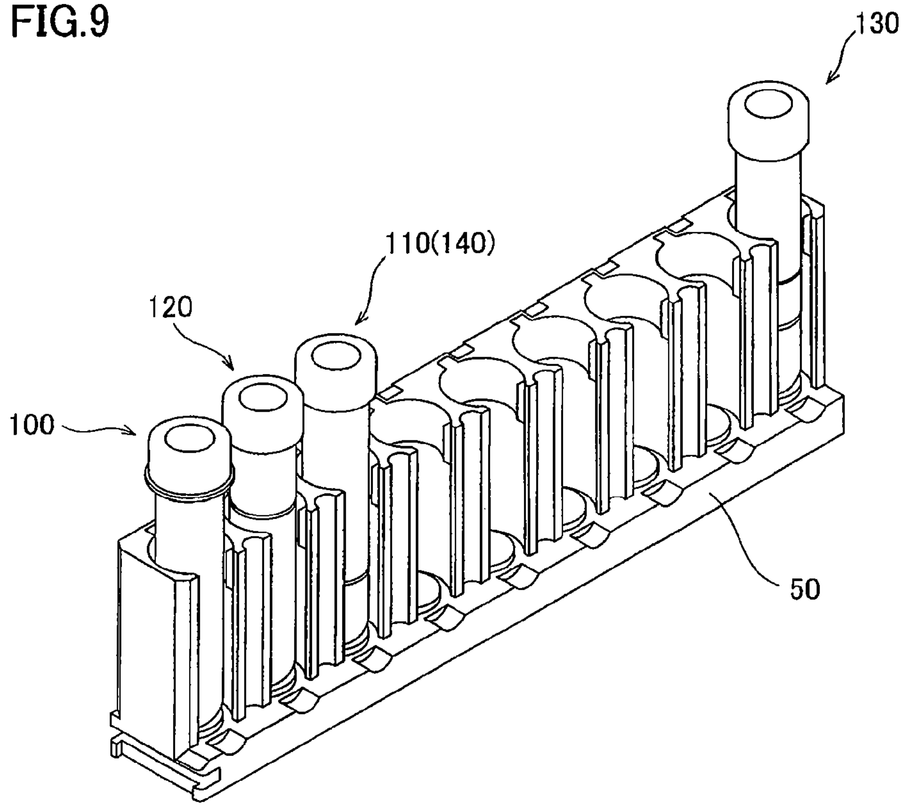
[FIG. 9] A perspective view showing a usage example of the specimen container in each of the first to fourth embodiments of the present invention.

The specimen container 110 has a height H (mm) of at least about 70 mm and not more than about 80 mm and a width (outer diameter) W of at least about 12 mm and not more than about 15 mm, as shown in FIGS. 1 and 3. These dimensions are nearly the same as those of a specimen container 100 (see FIGS. 9 and 10) for storing a patient specimen, having a normal volume. As shown in FIG. 9, the specimen container 110 is circularly formed in plan view.

Figure 10:
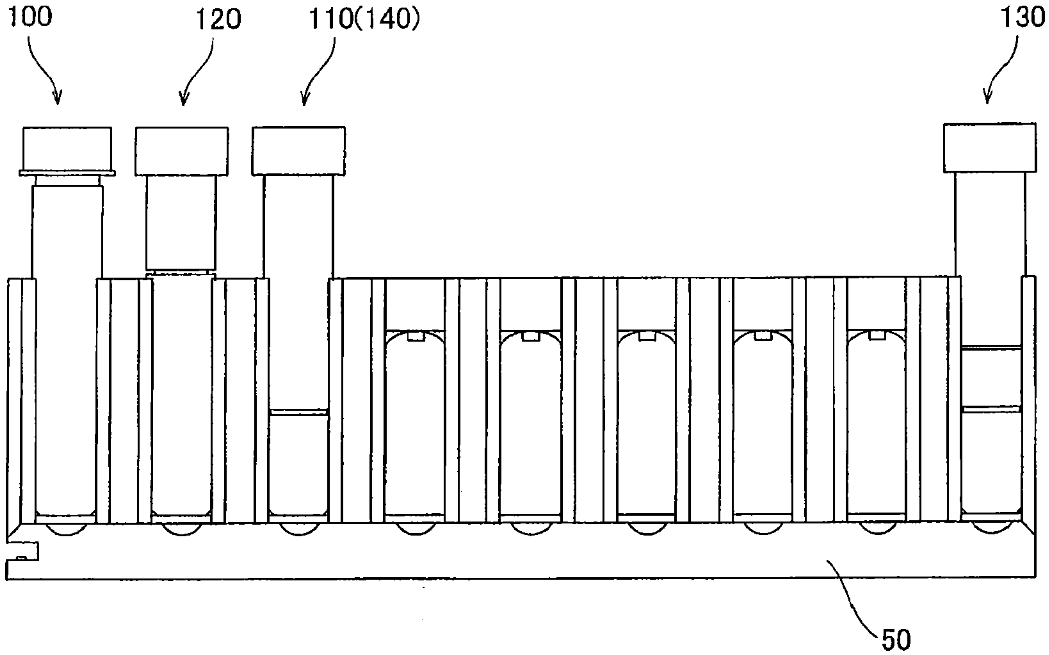
[FIG. 10] A front elevational view showing a usage example of the specimen container in each of the first to fourth embodiments of the present invention.

A bar code label 10 having information for identifying a stored specimen is stuck on an outer peripheral surface of the specimen container 110, as shown in FIG. 1. The specimen container 110 is supplied to an automatic blood cell counter 60 (see FIG. 11) in a state of being placed on a specimen rack 50 together with the normal specimen container 100 storing the patient specimen, as shown in FIGS. 9 and 10. The bar code labels 10 of the specimen containers 100 and 110 are formed to be read by a bar code reader 65 of the automatic blood cell counter 60, and a control portion 63 determines the specimen samples stored in the specimen containers on the basis of the information. When determining that the specimen stored in the specimen container is the control sample, the results of measurement are employed for quality control.

Figure 2:
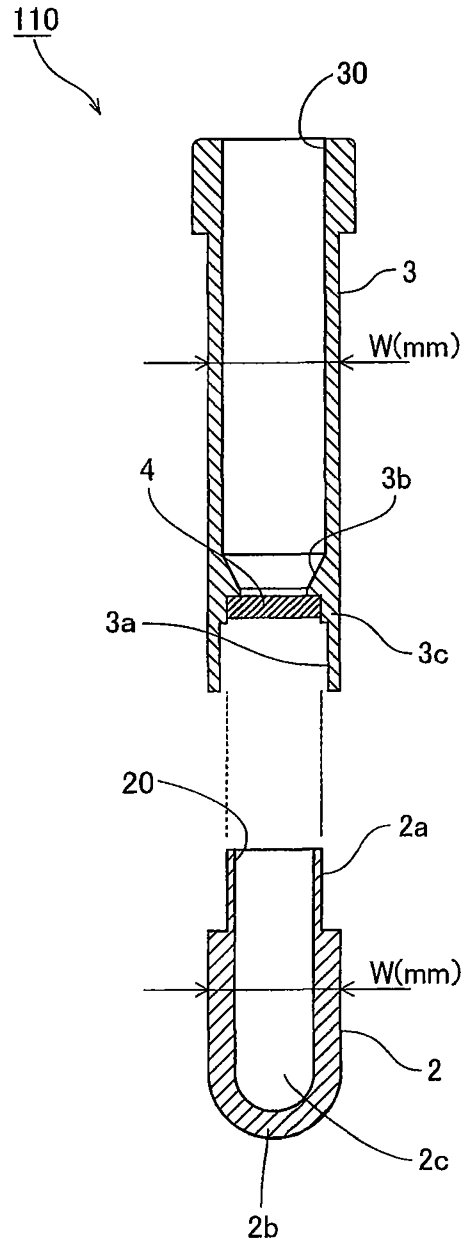
[FIG. 2] A sectional view showing an exploded state of the specimen container according to the first embodiment of the present invention.

As shown in FIG. 2, the container body 2 has the rounded bottom portion 2*b* and is a cylindrical container formed with an opening 20 on an upper end. As shown in FIG. 3, the inside thereof serves as a specimen storing portion 2*c* for storing the control sample 200. The container body 2 is made of hard plastic such as polyethylene terephthalate (PET). The container body 2 has a helical male screw portion 2*a* formed to protrude to the outside of the container body 2 in the vicinity of the opening 20 on the upper end. The male screw portion 2*a* of the container body 2 is fitted with a female screw portion 3*a*, described layer, provided on the cylindrical body 3, so that the container body 2 and the cylindrical body 3 are coupled. The container body 2 is so formed that the outer diameter has substantially the same size as the width (outer diameter) W of the specimen container. A thickness of the container body 2 is thicker than a thickness of the cylindrical body 3 and the container body 2 is so formed that a stored volume is much smaller, as shown in FIGS. 2 and 3. In other words, an inner diameter of the container body 2 is smaller than that of the cylindrical body 3. The thickness of a portion, formed with the male screw portion 2*a*, of the container body 2 is smaller than that of other portion of the container body 2.

The cylindrical body 3 is cylindrically formed and has a through-hole continuing from a lower side end to an upper side end. The cylindrical body 3 is made of hard plastic similarly to the container body 2. The cylindrical body 3 has the female screw portion 3*a* fitted with the male screw portion 2*a* of the container body 2 in the vicinity of the lower side end. More specifically, the helical female screw portion 3*a* is formed on an inner peripheral surface in the vicinity of the lower side end to be fitted with the male screw portion 2*a*. An opening 30 through which the suction tube is inserted is provided on the upper side end of the cylindrical body 3.

A holding portion 3*b* formed to partially have a thicker thickness is provided on the inside of the cylindrical body 3 above the female screw portion 3*a*, and the sealing member 4 is held on the inside of the cylindrical body 3 by this holding portion 3*b*. More specifically, the holding portion 3*b* is tapered to gradually increase the thickness from the upper side toward the lower side. In other words, the inner diameter of the cylindrical body 3 is conically gradually reduced by the holding portion 3*b*. A sealing member arrangement portion 3*c* formed to have a thickness larger than that in the vicinity of the lower side end of the cylindrical body 3 and smaller than that of a portion having the smallest inner diameter of the cylindrical body 3 by the holding member 3*b* is provided on the lower side of the portion having the smallest inner diameter of the cylindrical body 3. The sealing member 4 is arranged on the sealing member arrangement portion 3*c* to seal the through-hole of the cylindrical body 3. According to this structure, when the container body 2 is mounted on the cylindrical body 3, the upper end of the container body 2 is in contact with the sealing member 4, and hence the opening 20 on the upper end is sealed by the sealing member 4. Further, the vicinity of the opening 30 of the cylindrical body 3 is annularly formed to have a thicker thickness, and the outer diameter of the thicker portion is larger than that of other portions of the cylindrical body 3. In other words, the annular thicker portion protrudes outward beyond other portion of the cylindrical body 3. Thus, the annular thicker portion serves as a hooking portion when taking out the specimen container 110 placed on the specimen rack 50 (see FIGS. 9 and 10), for example, and the specimen container 110 is easily taken out.

A height of the cylindrical body 3 is so adjusted that a height of the specimen container in a state where the cylindrical body 3 is coupled with the container body 2 is substantially the same as the height H (mm) of the normal specimen container 100 storing the patient specimen. The specimen container 100 constituted by the container body 2 and the cylindrical body 3 is so formed that the width (outer diameter) thereof is substantially the same as the width (outer diameter) W of the normal specimen container 100. Thus, the external dimensions such as the height or the diameter of the specimen container 110 are nearly similar to those of the normal specimen container 100.

The sealing member 4 is made of an elastic material such as silicon rubber, for example, and is formed to have a larger diameter than the opening 20 of the container body 2, as shown in FIGS. 2 and 3. The sealing member 4 has a flat discoidal shape. The sealing member 4 is held on the inside of the cylindrical body 3 by the sealing member arrangement portion 3*c*. As shown in FIG. 3, when the container body 2 and the cylindrical body 3 are coupled by fitting the male screw portion 2*a* with the female screw portion 3*a*, the sealing member 4 is pressed upward from the lower side by the upper end of the container body 2, and upward movement of the cylindrical body 3 is regulated by the holding portion 3*b*. In other words, vertical movement is restricted in a state where the sealing member 4 is held between the holding portion 3*b* and the container body 2. Thus, the sealing member 4 is firmly supported so as not to slip off when puncturing the suction tube from above. The sealing member 4 is interposed between the holding portion 3*b* of the cylindrical body 3 and the container body 2 in the state where the cylindrical body 3 and the container body 2 are coupled, and the opening 20 of the container body 2 is sealed by the sealing member 4.

When the container body 2 is in a sealed state by coupling the container body 2 and the cylindrical body 3, the sealing member 4 is arranged at a position of about 40% from the bottom portion 2*b* with respect to the height H (mm) of the specimen container 110 (position of about 0.4 H (mm) from the bottom portion 2*b*), as shown in FIG. 3. Thus, even when the sample in the specimen container 110 is stirred in a state where a small quantity of specimen is stored, the moving quantity of the sample in the specimen container 110 is extremely small and damage to the specimen sample can be suppressed.

The control sample 200 is stored in the specimen storing portion 2*c* of the container body 2. The control sample 200 is analyzed by the automatic analyzer to be employed for providing quality control information, and the type thereof is not restricted so far as it contains a known quantity of a predetermined component. As the control sample 200, control blood containing a predetermined quantity of a predetermined blood component can be listed, for example. As the predetermined blood component, red blood cells including reticulocytes and nucleated red blood cells, blood platelets including reticulated platelets, and white blood cells including lymphocytes, monocytes, neutrophiles, eosinophiles and basophiles can be listed. These components may be obtained by purifying blood collected from an organism, or may be pseudo components artificially prepared. These blood components are suspended in a predetermined suspending solution. The suspending solution is a solvent isotonic to a blood component set to at least pH about 6.5 and not more than about 8.5, for example. The suspending solution may be a suspending solution containing a buffering agent, an antioxidant, a protein or a mixture of these, such as a phosphate buffer solution having magnesium gluconate/ethylenediaminetetraacetate (EDTA)/nucleated red blood cells; the same buffering agent containing additive HDL, sulfasalazine and alpha-tocopherol; or a buffering agent containing a small quantity of albumin, for example, in such an isotonic solvent.

While the quantity of the control sample 200 shown in FIG. 3 is less than half the volume of the specimen storing portion 2*c*, the quantity of the control sample 200 is preferably at least about 80% of the volume of the specimen storing portion 2*c* in a state before suction (non-suction state), and more preferably at least 90% of the volume of the specimen storing portion 2*c*. According to this structure, the moving quantity of the control sample 200 in the specimen storing portion 2*c* can be further reduced.

As hereinabove described, in the specimen container 110, the external height as the overall container is the height H (mm) identical with the normal specimen container 100 for storing the patient specimen, as shown in FIGS. 9 and 10. Further, a depth of the specimen container 110 from the upper end to the bottom portion 2*b* is substantially the same as that of the normal specimen container 100. Therefore, a depth for inserting the suction tube can be substantially the same as a depth in a case of inserting it into the normal specimen container 100, and hence no separate adjustment for the specimen container 110 storing the control sample 200 or the like is required. Thus, measurement of the control sample 200 or the like stored in the specimen container 110 can be performed by the automatic blood cell counter 60 without particular change of the automatic blood cell counter 60, similarly to measurement of the specimen stored in the normal specimen container 100. Furthermore, the specimen container 110 has a sufficient height, whereby the bar code label 10 can be stuck on the outer side surface of the specimen container 110, as shown in FIG. 1.

Second Embodiment

Figure 4:
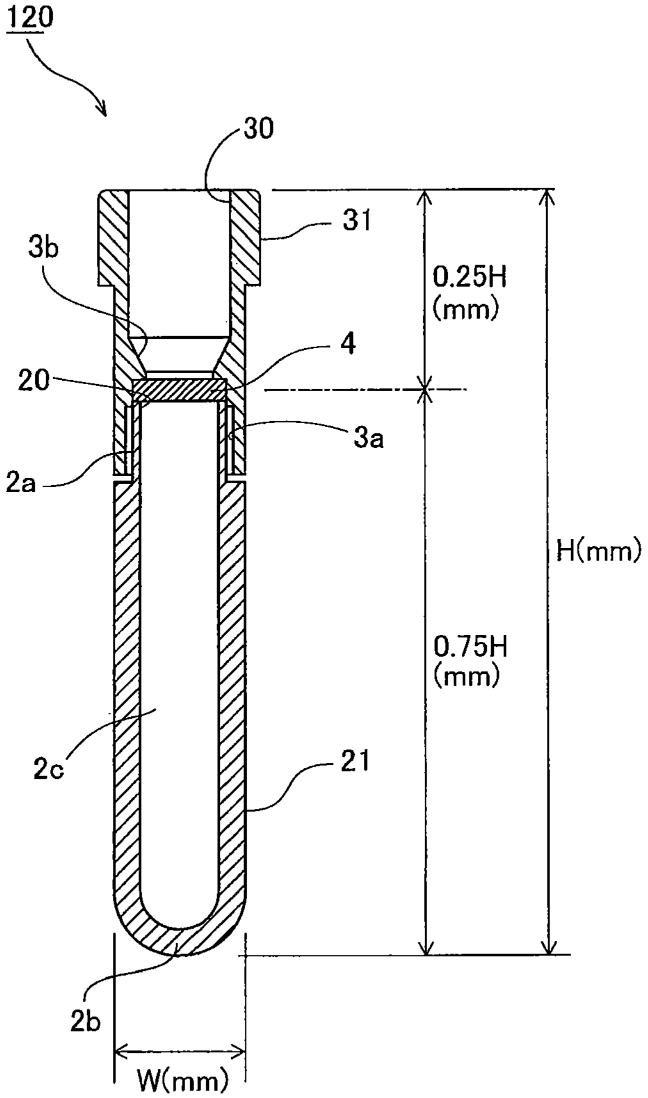
[FIG. 4] A sectional view of a specimen container according to a second embodiment of the present invention.

A specimen container 120 according to a second embodiment of the present invention will be now described with reference to FIGS. 3 and 4. As shown in FIG. 4, this specimen container 120 is so formed that a container body 21 has a volume larger than that of the container body 2 of the specimen container 110 according to the first embodiment dissimilarly to the specimen container 110 (see FIG. 3) according to the first embodiment of the present invention described above.

The specimen container 120 according to the second embodiment comprises the container body 21 having a length larger than that of the container body 2 in the aforementioned first embodiment, a cylindrical body 31 having a smaller length than the cylindrical body 3 in the aforementioned first embodiment and a sealing member 4. More specifically, the specimen container 120 has substantially the same height H (mm) as that of the normal specimen container 100 similarly to the specimen container 110 according to the aforementioned first embodiment, and the heights of the container body 21 and the cylindrical body 31 are so adjusted that a position of the sealing member 4 is arranged at a position of about 75% from a bottom portion 2*b* with respect to the height H (mm) of the specimen container 120 (position of about 0.75 H (mm) from the bottom portion 2*b*). This increases the volume of the container body 21.

The remaining structure of the specimen container 120 according to the second embodiment is similar to that of the aforementioned first embodiment.

According to the second embodiment, as hereinabove described, the specimen container comprising the container body 21 having the volume different from the container body 2 in the aforementioned first embodiment is prepared, whereby a more suitable specimen container can be selected depending on the quantity or the intended use of the specimen sample.

The remaining effects of the second embodiment are similar to those of the aforementioned first embodiment.

Third Embodiment

Figure 5:
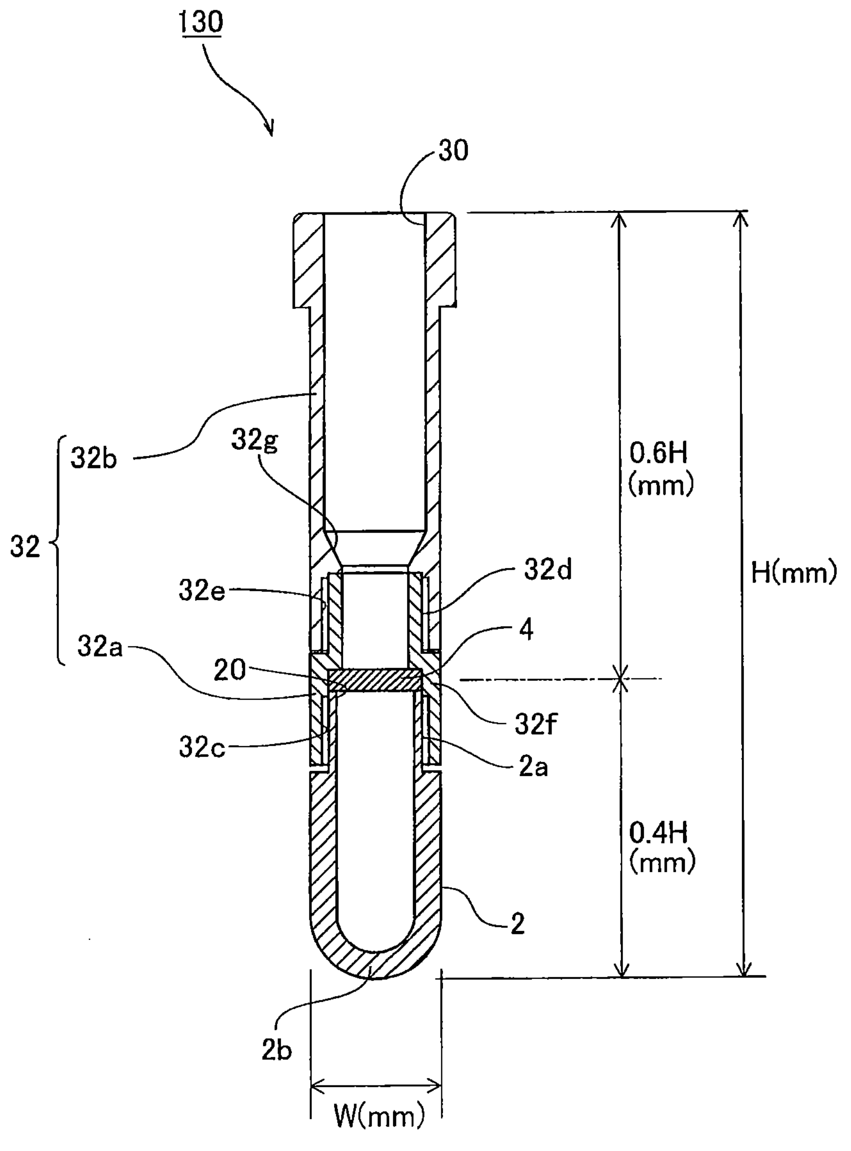
[FIG. 5] A sectional view of a specimen container according to a third embodiment of the present invention.

A specimen container 130 according to a third embodiment of the present invention will be now described with reference to FIGS. 3 and 5. As shown in FIG. 5, in this specimen container 130, a cylindrical body 32 is constituted by two members of a first cylindrical body 32*a* and a second cylindrical body 32*b* dissimilarly to the specimen container 110 (see FIG. 3) according to the first embodiment of the present invention described above.

The specimen container 130 according to the third embodiment comprises a container body 2, the cylindrical body 32 and a sealing member 4, as shown in FIG. 5. The cylindrical body 32 is constituted by the first cylindrical body 32*a* holding the sealing member 4 and the second cylindrical body 32*b* mounted on the first cylindrical body 32*a*. The first cylindrical body 32*a* has a female screw portion 32*c* fitted with a male screw portion 2*a* provided on the container body 2 in the vicinity of a lower side end. More specifically, the helical female screw portion 3*a* is formed on an inner peripheral surface in the vicinity of the lower side end to be fitted with the male screw portion 2*a* of the container body 2. The container body 2 and the first cylindrical body 32*a* are coupled by fitting them with each other.

A helical male screw portion 32*d* is formed on an upper side end side of the first cylindrical body 32*a* similarly to the male screw portion 2*a* formed on the container body 2, and the first cylindrical body 32*a* is coupled with the second cylindrical body 32*b* by fitting the male screw portion 32*d* with a female screw portion 32*e*, described later, of the second cylindrical body 32*b*.

The first cylindrical body 32*a* is cylindrically formed and has a through-hole continuing from the lower side end to the upper side end. The first cylindrical body 32*a* includes a holding portion 32*f* formed to have a thicker thickness than other portion in the vicinity of a center in a height direction. More specifically, the holding portion 32*f* is formed in a stepwise manner, and an inner diameter of the first cylindrical body 32*a* increases from the upper side toward the lower side in two stages by the stepwise holding portion 32*f*.

The sealing member 4 is held at a position having the second largest inner diameter of the holding portion 32*f* to block a through-hole of the first cylindrical body 32*a*. As shown in FIG. 5, when the container body 2 and the first cylindrical body 32*a* are coupled by fitting the male screw portion 2*a* with the female screw portion 32*c*, the sealing member 4 is pressed upward from the lower side by the upper end of the container body 2, and upward movement of the cylindrical body 3 is regulated by a step of the holding portion 32*f*. In other words, vertical movement is restricted in a state where the sealing member 4 is held between the step of the holding portion 32*f* and the container body 2. Thus, the sealing member 4 is firmly supported so as not to slip off when puncturing a suction tube from above.

The second cylindrical body 32*b* is cylindrically formed, and has a through-hole continuing from a lower side end to an upper side end. The helical female screw portion 32*e* capable of fitting with the male screw portion 32*d* of the first cylindrical body 32*a* is formed on the lower side end of the second cylindrical body 32*b*. An opening 30 through which the suction tube is inserted is provided on the upper side end of the second cylindrical body 32*b*. A tapered portion 32*g* provided on an upper side of the female screw portion 32*d* of the second cylindrical body 32*b* is so formed in a tapered shape that an inner diameter of the second cylindrical body 32*b* is gradually reduced downward from the upper side. The tapered portion 32*g* is so formed that a portion having the smallest inner diameter of the second cylindrical body 32*b* has nearly the same inner diameter as the upper side end of the first cylindrical body 32*a*.

The remaining structure of the specimen container 130 according to the third embodiment is similar to that of the aforementioned first embodiment.

The effects of the third embodiment are similar to those of the aforementioned first embodiment.

Fourth Embodiment

A specimen container 140 according to a fourth embodiment of the present invention will be now described with reference to FIG. 3 and FIGS. 6 to 8. As shown in FIG. 7, this specimen container 140 comprises a lid body 40 formed to enter a container body 2 and be fitted into the container body 2 along an inner surface of the container body 2 as a sealing member, dissimilarly to the specimen container 110 (see FIG. 3) according to the first embodiment of the present invention described above.

Figure 6:
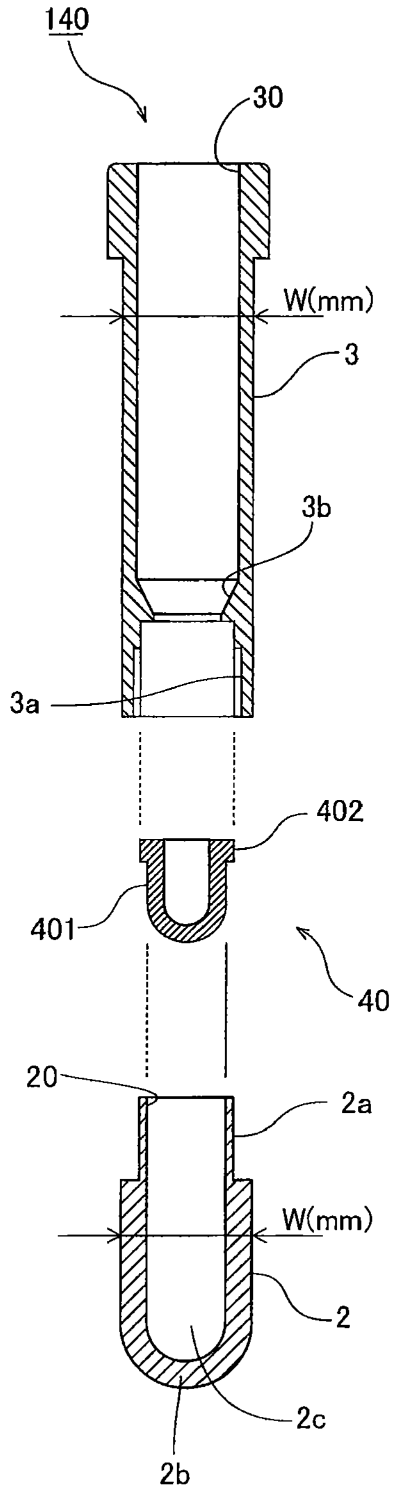
[FIG. 6] A sectional view showing an exploded state of a specimen container according to a fourth embodiment of the present invention.
Figure 7:
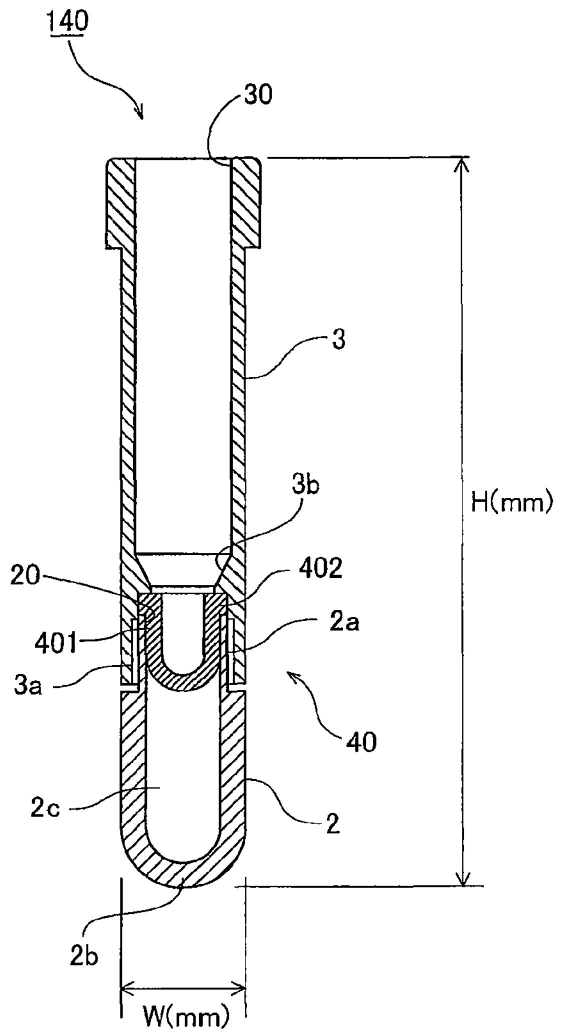
[FIG. 7] A sectional view of the specimen container according to the fourth embodiment of the present invention.

As shown in FIG. 6, the specimen container 140 comprises the container body 2, a cylindrical body 3 and the lid body 40 serving as the sealing member.

The lid body 40 is made of an elastic member such as silicon rubber, for example, and includes a stopper portion 401 fitted into an opening 20 of the container body 2 and sealing the container body and a stop ring portion 402 annularly formed to protrude outward from the stopper portion 401. The lid body 40 is circularly formed in plan view.

The stopper portion 401 is formed to protrude downward, and is so formed that an outer diameter has substantially the same size as the inner diameter of the container body 2 in plan view. Thus, when the lid body 40 is fitted into the container body 2, an outer side surface of the stopper portion 401 is in contact with an inner side surface of the container body 2 and the container body 2 can be sealed.

The stop ring portion 402 is formed to be in contact with an edge (upper end surface of the container body 2) of the opening 20 of the container body 2 in a state where the stopper portion 401 is fitted into the container body 2. Thus, the lid portion 40 can be prevented from slipping off in the container body 2 when a suction tube punctures downward from above. As shown in FIG. 7, the stop ring portion 402 is held between the edge of the opening 20 of the container body 2 and the holding portion **3*b* of the cylindrical body 3 in a state where the container body 2 and the cylindrical body 3 are coupled, and hence the lid body 40 is firmly supported against the puncture of the suction tube. The cylindrical body 3 may be mounted on the lid body 40**.

The remaining structure of the specimen container 140 according to the fourth embodiment is similar to that of the aforementioned first embodiment.

Figure 8:
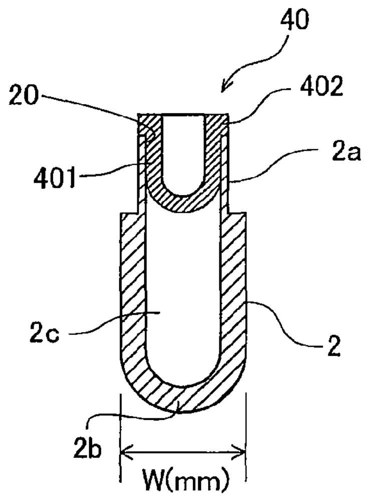
[FIG. 8] A sectional view showing a state of the specimen container, which is not mounted with a cylindrical body, according to the fourth embodiment of the present invention.

According to the aforementioned fourth embodiment, as hereinabove described, the lid body 40 serving as the sealing member is provided and the stopper portion 401 of the lid body 40 is so formed that the outer diameter is substantially the same as the inner diameter of container body 2, whereby the outer side surface of the stopper portion 401 is in contact with the inner side surface of the container body 2, and the container body 2 is sealed by the lid body 40, and hence the cylindrical body 3 may not be mounted on the container body 2 in order to seal the container body 2. Thus, the specimen stored in the container body 2 can be preserved or carried in a state of only the container body 2 sealed by the lid body 40, having a small height as shown in FIG. 8, and hence the specimen can be easily handled.

According to the fourth embodiment, the lid body 40 as the sealing member, sealing the opening 20 is provided to be fitted into the container body 2, whereby the lid body 40 enters the container body 2, and hence a stored volume of the container body 2 can be reduced.

The remaining effects of the fourth embodiment are similar to those of the aforementioned first embodiment.

Figure 11:
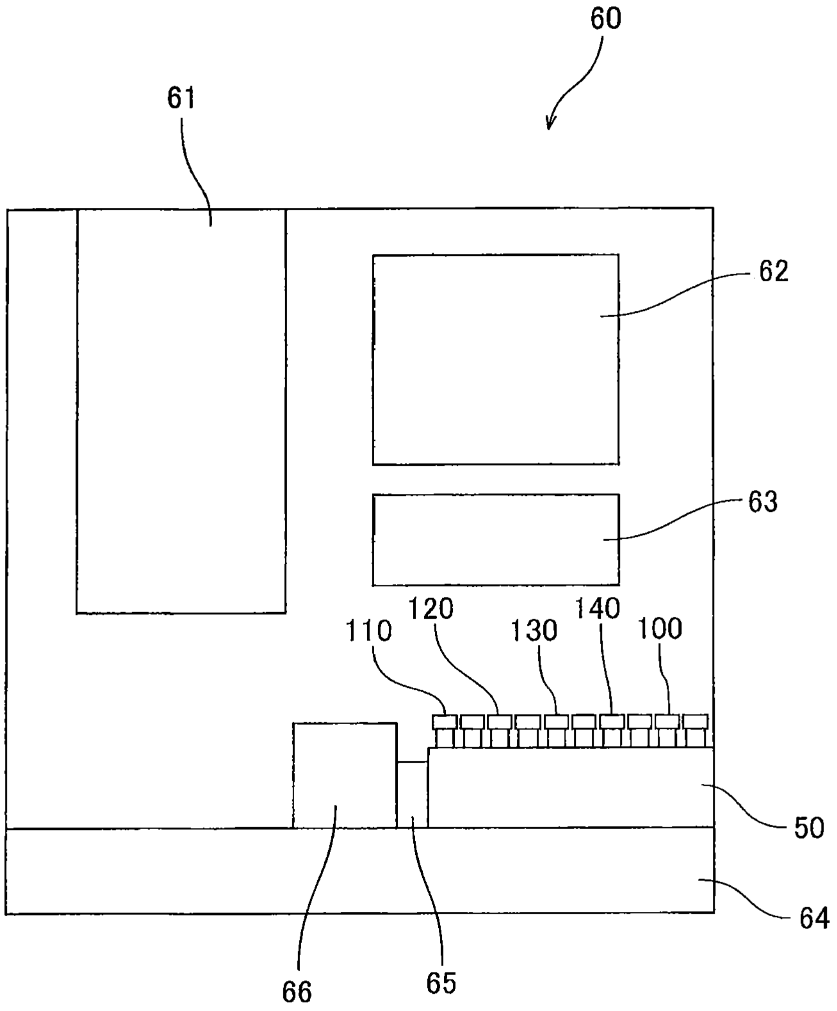
[FIG. 11] A schematic configuration diagram showing a usage example of supplying the specimen container in each of the first to fourth embodiments of the present invention to an automatic analyzer.

An specimen measuring operation by the automatic blood cell counter 60, employing the specimen containers 110, 120, 130 and 140 according to the first to fourth embodiments and the normal specimen container 100 will be now described with reference to FIGS. 9 to 11. In FIGS. 9 to 11, bar code labels are not illustrated in order to recognize difference in shapes of the specimen containers 100, 110, 120, 130 and 140 (hereinafter referred to as the specimen container 100 and the like).

The specimen containers 110, 120, 130 and 140 (hereinafter referred to as the specimen container 110 and the like) according to the first to fourth embodiments are placed on a specimen rack 50 vertically holding the plurality of specimen containers and supplied to the automatic blood cell counter 60 (see FIG. 11), similarly to the normal specimen container 100. As apparent from FIGS. 9 and 10, external dimensions (height H and width (outer diameter) W) of the specimen container 110 and the like are substantially the same as the normal specimen container 100. Thus, the specimen container 110 and the like can be placed on the specimen rack 50 completely similarly to the normal specimen container 100, and an operation of grasping or an operation of stirring the specimen by the automatic blood cell counter 60 can be performed similarly to the normal specimen container 100. Further, the height from an upper end to a bottom portion of each of the specimen container 110 and the like is similar to that of the normal specimen container 100, and hence an operation of inserting the suction tube by the automatic blood cell counter 60 can be also performed similarly to the normal specimen container 100.

The automatic blood cell counter 60 is an automatic blood cell counter capable of automatically analyzing blood components, and comprises a sample analysis portion 61, a display operating portion 62 inputting analysis conditions or outputting results of measurement, and a control portion 63 constituted by a CPU and a memory (not shown), as shown in FIG. 11. The sample analysis portion 61 includes a rack supply portion 64 supplying a plurality of the specimen racks 50 placed with the specimen container 100 and the like to a predetermined position one by one, a bar code reader 65 for reading the bar code label 10 (see FIG. 1) stuck on each of the specimen container 100 and the like, a sample stirring/suction portion 66 for stirring/sucking the specimen sample stored in each of the specimen container 100 and the like, a sample quantitative determination portion determining the quantity of the sucked sample, a sample preparation portion preparing a measurement sample and a sample measurement portion measuring the measurement sample (not shown).

The specimen measuring operation by the automatic blood cell counter 60 will be now described.

As shown in FIG. 11, the specimen rack 50 loaded with the specimen container 100 storing a specimen collected from a patient and the specimen container 110 and the like according to the first to fourth embodiments storing control samples 200 (see FIG. 3) is placed on the rack supply portion 64 of the automatic blood cell counter 60. When an operator inputs a measurement instruction from the display operating portion 62, the specimen rack 50 on the rack supply portion 64 moves in a direction of the sample stirring/suction portion 66 of the automatic blood cell counter 60. The bar code labels 10 of the specimen container 100 and the like in the moved specimen rack 50 are read by the bar code reader 65 on a route to the sample stirring/suction portion 66. The control portion 63 identifies the specimens stored in the specimen container 100 and the like on the basis of the results read by the bar code reader 65. Thereafter, the sample stirring/suction portion 66 stirs and sucks the specimens stored in the specimen container 100 and the like in the specimen rack 50 carried to the sample stirring/suction portion 66. The stirring operation is performed by repeatedly turning the specimen container 100 or the like upside down a predetermined number of times while grasping the specimen container 100 or the like. In the specimen container 100 or the like storing the specimen which was completed to be stirred, a nearly central portion of the sealing member 4 made of the elastic member is punctured on the sample stirring/suction portion 66 by a needle-shaped narrow tube for sample suction inserted through the opening 30 of the cylindrical body 3 (31, 32). Then, the narrow tube for sample suction passes through the sealing member 4, the forward end lowers to the vicinity of the bottom portion 2*b* of the container body 2 (21), and thereafter the specimen is sucked from the specimen container 100 or the like.

The quantity of the sucked specimen is determined by the sample quantitative determination portion of the sample analysis portion 61, and treatment such as dilution/hemolysis is performed by the sample preparation portion. Thereafter, the specimen is measured by the sample measurement portion, and measurement date is output to the display operating portion 62. The measurement data includes the number of red blood cells, hematocrit, mean red cell volume (MCV), the number of platelets (PLT), the number of white blood cells and the like. The results of measurement based on the control sample 200 are stored in time series and plotted to create a control chart by the control portion 63. Thus, dispersion (variation) of measurement values with time can be observed with reference to a plot obtained from the control sample 200, for example, and measurement precision of the apparatus can be precisely controlled.

While the position of the sealing member in coupling the container body with the cylindrical body is the position of about 40% from the bottom portion with respect to the height H (mm) of the specimen container (position of about 0.4 H (mm) from the bottom portion) in the first embodiment and the position of about 75% from the bottom portion with respect to the height H (mm) of the specimen container (position of about 0.75 H (mm) from the bottom portion) in the second embodiment, the present invention is not restricted to this but the position may be suitably changed so far as it is a position of at least 10% and not more than 80% from the bottom portion with respect to the height H (mm) of the specimen container. In this case, the sealing member is preferably arranged on a position of at least about 20% and not more that about 80% with respect to the height H (mm) of the specimen container, and the sealing member is more preferably arranged on a position of at least about 25% and not more that about 75% with respect to the height H (mm) of the specimen container.

Figure 12:
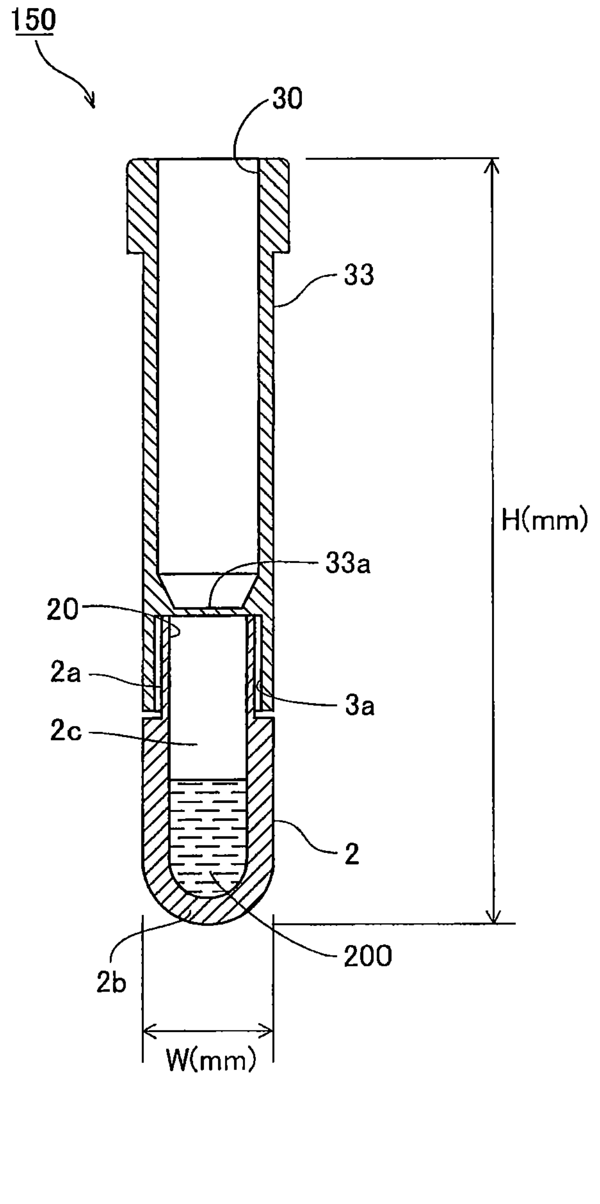
[FIG. 12] A sectional view for illustrating a modification of the specimen container in each of the first to fourth embodiments of the present invention.

While the cylindrical body and the sealing member (lid body) are separately formed in each of the aforementioned first to fourth embodiments, the present invention is not restricted to this but the cylindrical body and the sealing member (lid body) may be integrally formed. At this time, a specimen container 150 is preferably so formed that a thickness of a portion 33*a* corresponding to a sealing member of a cylindrical body 33 is thin in order to allow puncture by a suction tube, as shown in FIG. 12. The portion 33*a* corresponding to the sealing member can be provided with a notch for easy puncture.

While the container body and the cylindrical body are separately formed in each of the aforementioned first to fourth embodiments, the present invention is not restricted to this but the container body and the cylindrical body may be integrally formed. Such a specimen container is produced as follows, for example. First, at a position of a prescribed depth of a cylindrical specimen container having a bottom portion designed to have the same height H (mm) and the same width (outer diameter) W (mm) as the normal specimen container, a stop portion formed to protrude inward is provided on an inner side surface. Then, a discoidal sealing member formed to have a diameter identical with or slightly smaller than an inner diameter of the specimen container is inserted from an opening of the specimen container, and the sealing member is stopped on the stop portion provided at the prescribed depth of the specimen container. According to this structure, the specimen container for a small quantity of the specimen can be produced with a simple structure and a small number of components.

While the cylindrical body formed to be mounted on the container body is shown as an exemplary cylindrical body in the aforementioned fourth embodiment, the present invention is not restricted to this but it may be a cylindrical body formed to be mounted on the lid body fitted into the container body.

What is claimed is:

1. A specimen container comprising:

a specimen storing portion for storing a sample and comprising a first engaging portion, wherein said specimen storing portion is provided with an opening on an upper end;

a sealing member for sealing said opening, wherein said sealing member is made of an elastic material; and a cylindrical portion having a predetermined height to allow insertion of a suction tube and comprising a second engaging portion capable of being engaged to the first engaging portion, wherein said cylindrical portion is arranged in series with said specimen storing portion on said open end, wherein one of said first and second engaging portions has a male screw and another has a female screw, and said opening of said specimen storing portion is sealed from said cylindrical portion by said sealing member when said cylindrical portion and said specimen storing portion are engaged;

wherein said sealing member is fixed by being clipped by said specimen storing portion and said cylindrical portion.

2. The specimen container according to claim 1, wherein said sealing member is arranged on a position of at least 10% and not more than 80% from a bottom portion of said specimen storing portion with respect to a height of said specimen container.

3. The specimen container according to claim 1, wherein said cylindrical portion comprises an identifier having identification information for identifying a specimen stored in said specimen storing portion.

4. The specimen container according to claim 1 wherein said sealing member and said cylindrical portion are integrally formed at a holding portion.

5. A specimen container comprising:

a specimen storing portion for storing a sample and comprising a first engaging portion, wherein said specimen storing portion is provided with an opening on an upper end;

a sealing member for sealing said opening, wherein said sealing member is made of an elastic material; and a cylindrical portion having a predetermined height to allow insertion of a suction tube and comprising a second engaging portion capable of being engaged to the first engaging portion, wherein said cylindrical portion is arranged in series with said specimen storing portion on said open end, wherein one of said first and second engaging portions has a male screw and another has a female screw, and said opening of said specimen storing portion is sealed from said cylindrical portion by said sealing member when said cylindrical portion and said specimen storing portion are engaged;

wherein a height of said specimen container is at least 70 mm and not more than 80 mm.

6. A specimen container for storing a specimen analyzed by an analyzer, said specimen container comprising:

a container body, formed to be cylindrical, having an opening on an upper end and having a bottom portion on a lower end and comprising a first engaging portion;

a cylindrical body, mountable on said container body above said opening of said container body, comprising a second engaging portion capable of being engaged to the first engaging portion;

a sealing member, as part of the cylindrical body, for sealing a specimen stored in the specimen container, said sealing member is arranged on a predetermined position at said upper end of said container body and is made of an elastic material; and a lid body as said sealing member, for sealing said opening of said container body wherein said cylindrical body is mountable on said lid body; wherein one of said first and second engaging portions has a male screw and another has a female screw, and said opening of said container body is sealed by said sealing member when said cylindrical body and said container body are engaged.

7. The specimen container according to claim 6, wherein said sealing member is arranged on a position of at least 10% and not more than 80% from said bottom portion with respect to a height of said specimen container.

8. The specimen container according to claim 6 wherein said cylindrical body is mounted on said container body, so that said opening of said container body is sealed by said sealing member.

9. The specimen container according to claim 8, wherein said cylindrical body further comprises a holding portion for holding said sealing member.

10. The specimen container according to claim 1, wherein said cylindrical portion comprises a holding portion which holds said sealing member.

11. The specimen container according to claim 6, wherein said cylindrical body comprises a holding portion which holds said sealing member.

12. The specimen container according to claim 1, further comprising a control sample, employed for quality control of an analyzer for analyzing said specimen, as said specimen, wherein said control sample is previously stored in said specimen storing portion.

* * * * *